United States Patent [19]

Amaral et al.

[11] Patent Number: 4,850,992
[45] Date of Patent: Jul. 25, 1989

[54] FASTENING AND SEALING SYSTEM FOR DIAPERS

[75] Inventors: Everson Amaral; Rosana R. Das Neves, both of Sao Paulo, Brazil

[73] Assignee: Chicopee, New Brunswick, N.J.

[21] Appl. No.: 18,655

[22] Filed: Feb. 25, 1987

[30] Foreign Application Priority Data

Feb. 26, 1986 [BR] Brazil ................................. 8600823

[51] Int. Cl.[4] ........................................... A61F 13/16
[52] U.S. Cl. .................................. 604/389; 604/385.1
[58] Field of Search ............... 604/385 R, 385 A, 386, 604/387, 389, 390, 391

[56] References Cited

U.S. PATENT DOCUMENTS

| | | | |
|---|---|---|---|
| 2,714,889 | 8/1955 | Chambers | 604/390 |
| 3,610,244 | 10/1971 | Jones, Sr. | 604/390 |
| 3,990,449 | 11/1976 | Cheslow | 604/390 |
| 3,995,639 | 12/1976 | Cheslow | 604/390 |
| 4,014,339 | 3/1977 | Tritsch | 604/390 |
| 4,014,340 | 3/1977 | Cheslow | 604/390 |
| 4,033,348 | 7/1977 | Cepuritis | 604/390 |
| 4,615,695 | 10/1986 | Cooper | 604/394 |
| 4,680,030 | 7/1987 | Coates et al. | 604/391 |

Primary Examiner—C. Fred Rosenbaum
Assistant Examiner—Denise Whelton
Attorney, Agent, or Firm—Lawrence D. Schuler

[57] ABSTRACT

A disposable diaper comprising an absorbent core disposed between a liquid-impermeable backing sheet and a liquid-permeable facing sheet and having means for closing and fastening the diaper around the waist which are independent from means for sealing the diaper around the thighs of the wearer. The diaper employs two regions of adhesive for this purpose. The first said region is preferably located at the upper end of the diaper and comprises two adhesive areas at or near the corners of the diaper. The second adhesive region is located at the other end of the diaper and comprises two adhesive areas which are located in the side margins of the diaper and are spaced away from the corners at said other end. There are slits between the corners of the diaper and the adhesive areas of the second adhesive region. These slits extend inwardly from the side margins of the diaper toward its center.

6 Claims, 3 Drawing Sheets

FASTENING AND SEALING SYSTEM FOR DIAPERS

The present invention refers to absorbent articles and more specifically to closure or fastening and sealing systems for diapers.

The prior art has developed sealing systems directed to leak-prone regions by applying elastic elements as illustrated in U.S. Pat. Nos. 4,050,462 of Woon, 3,860,003 of Buell, 4,388,075 and 4,352,355 of Mesek et al.

Conventional prior art is mainly based on the use of adhesive tapes for closing or fastening diapers, especially disposable diapers, around the waist of the wearer. In addition, the prior art has provided sealing systems to prevent fluid from leaking from the diaper in the regions around the wearer's thighs and waist. Sealing systems which help prevent leakage in the thigh regions comprise elastic elements, such as elastic bands or one or more elastic strands, which are secured in the generally central portions of the side margins of the diaper.

Sealing systems which help prevent leakage of liquid at the waist of the wearer comprise elastic elements which are secured in the upper and/or lower margins of the diaper to provide a so-called "elasticized waistband" diaper. In the prior art, the aforementioned fastening or closure system and the aforementioned sealing system are interdependent and allowed, relative motion between the wearer's body and the diaper itself. This produced bagginess which in turn led to leakage of liquid especially at the leg regions of the diaper.

Therefore, there is a need for an improved diaper which diminishes or eliminates leakage.

The present invention proposes a solution to the problem by providing a diaper having a closure or fastening system which works independently of its sealing system, thus allowing an improved fitting of the diaper to the user's thighs independent from the fitting of the diaper to the user's waist, and reducing considerably the likelihood of leakage of liquid, especially in the regions around the wearer's legs.

In addition, the invention provides a better fitting of the diaper to the user's waist and thighs, which can vary according to each user'erogonomic characteristics. The user can move his legs without significantly affecting the relative position of the diaper to the body.

The above objects and others are achieved by providing on the diaper a first region of adhesive comprising two adhesive areas placed symmetrically with respect to the longitudinal axis of the diaper, there being one such area of adhesive at each upper corner of the diaper, and a second region of adhesive comprising two adhesive areas placed symetrically with respect to the longitudinal axis of the diaper, there being one such area of adhesive regions near the bottom of the diaper being spaced away from the corners therof toward the transverse central axis of the diaper.

The invention can be better understood with reference to the following detailed description together with the appended drawings in which.

DESCRIPTION OF THE PREFERRED EMBODIMENT

Figure 2:
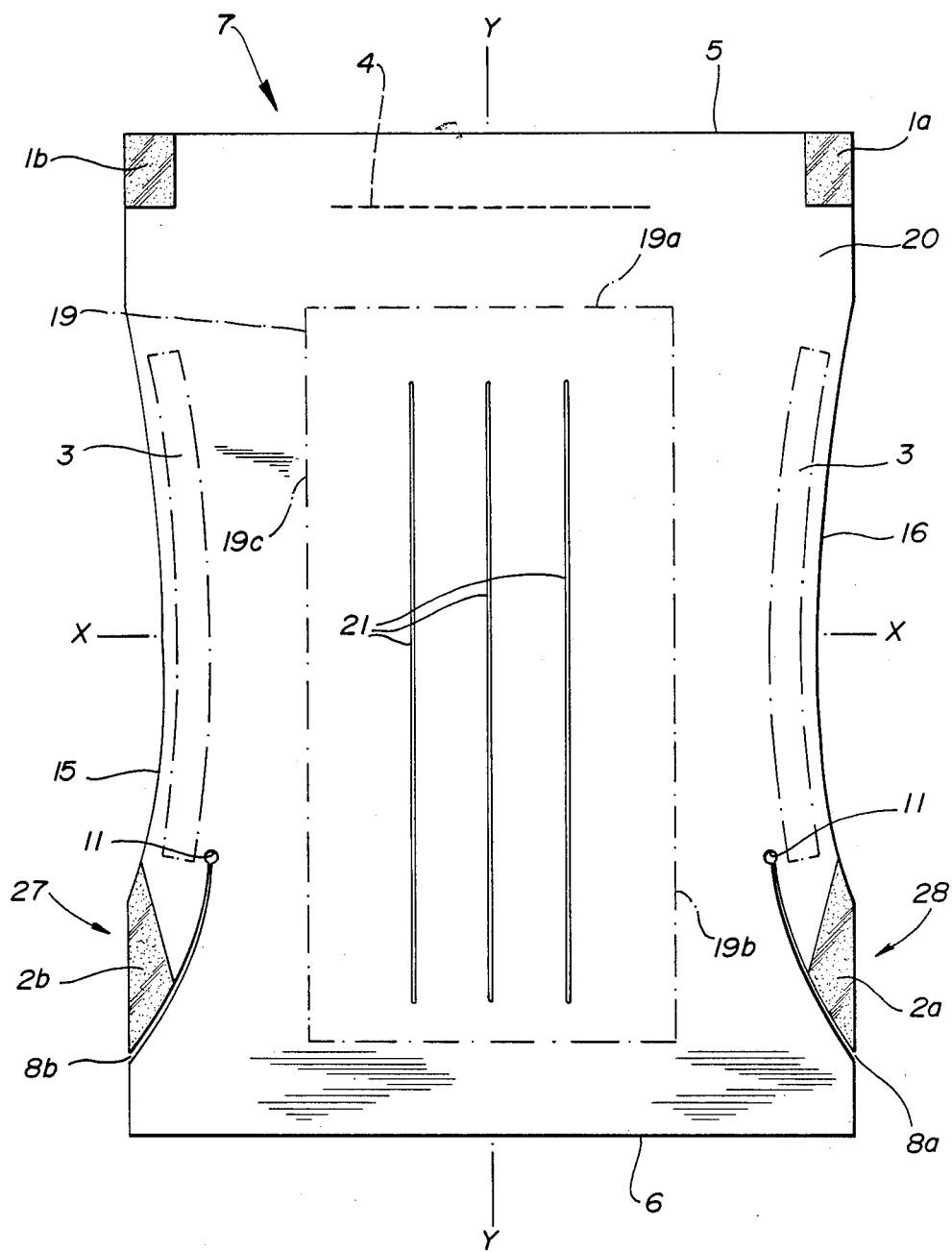
FIG. 2 is a top plan view of the diaper of FIG. 1 in its flat condition.

Referring especially to FIG. 2, it will be seen that diaper 7 has a central transverse axis, X-X, located midway between and parallel to its upper edge 5 and lower edge 6 and a central longitudinal axis, Y-Y, located midway between its opposed side edges 15, 16, and intersecting the transverse axis at right angles. Diaper 7 comprises a liquid-impermeable backing sheet 18, an absorbent core 19 for absorbing and holding liquid, such as urine, and a liquid-permeable facing or covering sheet 20. Backing sheet 18 is preferably a film of polyethylene or the like while absorbent core 19 comprises a batt of highly absorbent fibers such as comminuted wood pulp fibers. The absorbent core may be embossed along lines 21 to improve its stability. Facing sheet 20, which contacts the wearer's body when the diaper is in use, preferably comprises a liquid-permeable nonwoven fabric, although other covering materials, for example, a highly liquid-porous paper may also be used. Drape 7 further comprises an elastic element 4, in the form of one or more elastic monofilaments, secured between the backing sheet and the facing sheet in the upper margin of the diaper to provide an elasticized waistband position. Similar elastic elements may be provided in the marginal end portion of the diaper adjacent lower edge 6. Elastic elements 3,3 are provided in the central portions of the left and right side margins of the diaper to provide a gasketing effect in those portions of the diaper which, when the diaper is used, will surround the thigh regions of the wearer. Elastic elements 3,3 are preferably in the form of tapes but one or more monofilaments may be used if so desired.

The backing sheet and facing sheet are substantially coextensive and are secured to each other in the marginal portions of the diaper by, e.g., a plurality of glue lines (not shown in the drawings) running parallel to longitudinal axis, Y-Y. If desired, absorbent core may be stabilized in its position between the backing and facing sheets by securing it with lines of adhesive to the underlying backing sheet.

The upper margin of the diaper, i.e., that portion lying generally between upper edge 5 of the diaper and upper edge 19a of the absorbent batt, has a first region of pressure sensitive adhesive which comprises a generally rectangular adhesive area 1a at the upper right hand corner of the diaper and a generally rectangular adhesive area 1b at the upper left hand corner. The lower portion of the diaper, i.e., that portion thereof which is nearer lower edge 6, has a second region of pressure sensitive adhesive which comprises adhesive area 2a and adhesive area 2b. Adhesive area 2a is located in the right side margin of the diaper, i.e., that portion thereof which lies between right side edge 16 of the diaper and the extended right side edge 19b of absorbent core 19, and is spaced a short distance upwardly, i.e. in the direction toward transverse axis, X-X, from lower edge 6. Adhesive area 2b is located in the left side margin of the diaper, i.e. that portion thereof which lies between left side margin 15 and the extended left side edge 19c of absorbent core 19, and is also spaced a short distance upwardly, in the same fashion as adhesive area 2a, from lower edge 6 of the diaper. As can be appreciated from reference to FIG. 2 of the drawings, adhesive areas 1a, 1b, 2a and 2b are applied, e.g. by an adhesive transfer process, to the exposed surface of covering sheet 20. The adhesive areas are preferably covered with removable protective sheets which protect them from dust and the like prior to their actual use. The adhesive is preferably of the type which can be released from the surface of backing sheet 18 without damage to either the adhesive or backing sheet. Alternatively, the backing sheet can be provided with "landing areas" in the regions where it will be contacted by adhesive portions 1a, 1b, 2a and 2b when the diaper is in use. These "landing areas" could be, e.g., strips of paper secured to the backing sheet with the exposed upper surface of said strips being treated, e.g., with a suitable release agent, to allow easy release of the adhesive therefrom when it is desired to adjust or remove the diaper.

It will be understood that adhesive areas 1a and 1b can be moved slightly downwardly from upper edge 5 or slightly inwardly from side edges 16 and 15, respectively. Adhesive areas 2a and 2b can be shifted slightly inwardly from side edges 16 and 15, respectively, of the diaper.

Diaper 7 further comprises a pair of slits, 8a and 8b, in the lower portions of the right and left hand margins, respectively, and arranged generally symmetrically with respect to longitudinal axis, Y-Y. Slit 8a is preferably arcuate in shape and extends inwardly and toward transverse axis, X-X, from a point on the right side edge 16 of the diaper which lies between adhesive area 2a and the point of juncture of right side edge 16 and lower edge 6 of the diaper.

Slit 8b has the same arcuate configuration as slit 8a and extends inwardly and toward transverse axis, X-X, from a point on the left side edge 15 of the diaper which lies between adhesive area 2b and the point of juncture of left side edge 15 and lower edge 6 of the diaper. The distance between lower edge 6 and the points where slits 8a and 8b meet side edges 16 and 15, respectively, should be at least equivalent to the length, measured parallel to longitudinal axis, Y-Y, of adhesive areas 1a and 1b.

In the diaper illustrated in FIG. 2, slits 8a and 8b terminate in a circular opening 11 located near elastic element 3 and inwardly of side edges 16 and 15 respectively, of the diaper. It will be understood that the radius of curvature of slits 8a and 8b may be varied and that these slits could be straight, if desired. in any event, when slits 8a and 8b are provided as aforesaid, flaps 27 and 28 are formed at the side margins of the diaper, with adhesive area 2a being applied to and carried by flap 28 and adhesive area 2b being applied to and carried by flap 27.

Figure 1:
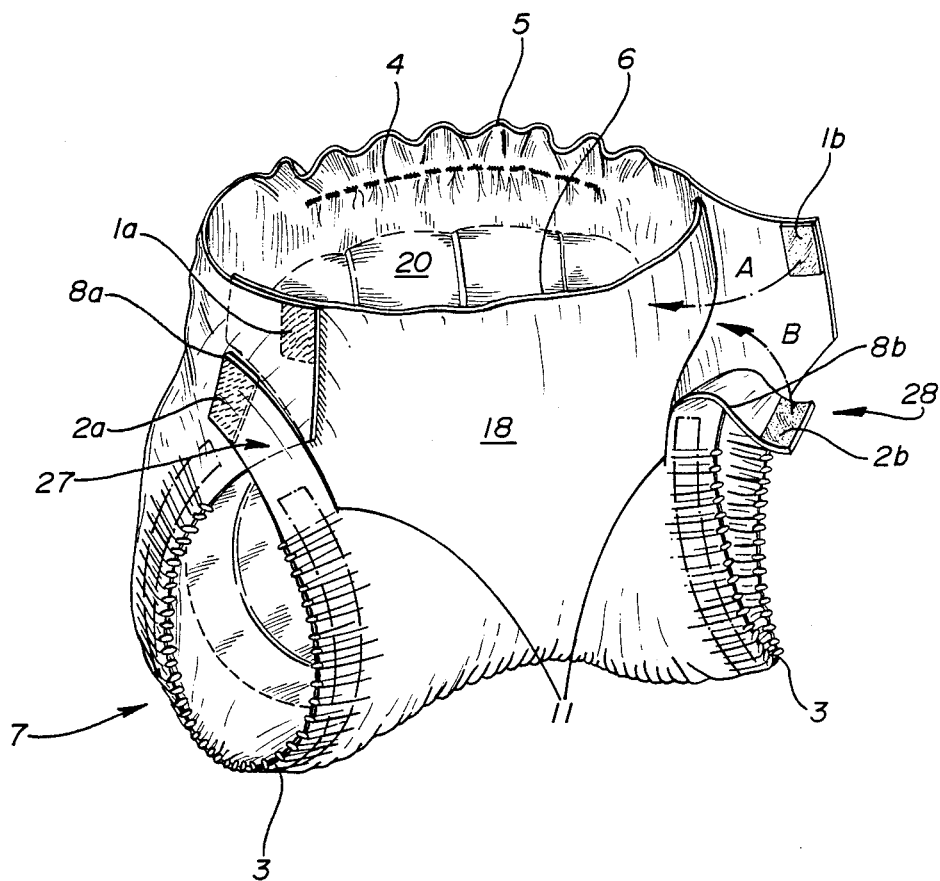
FIG. 1 is a perspective view of a diaper incorporating the principles of the present invention, said diaper being shown in the general configuration it would assume when being worn by the user.

In use, a child to be diapered is positioned facing upwardly on top of the diaper in the generally flat configuration shown in FIG. 2 so that the child's buttocks are disposed more or less centrally of the diaper. The lower part of the diaper is brought up between the child's leg so that lower edge 6 is in alignment with upper edge 5. Adhesive areas 1a and 1b at upper edge 5 are inserted into slits 8a and 8b, respectively, and adhered to the backing sheet at the corner regions where side edges 16 and 15, respectively, meet lower edge 6. This action fixes the diaper in position around the child's waist. Flaps 27 and 28 are manipulated to conform the diaper around the thighs of the child and are then secured, by way of adhesive areas 2b and 2a respectively, to the impermeable backing sheet 18. This sequence is illustrated at the right hand side of FIG. 1 where flap 28 has been moved aside so that adhesive area 1b can be inserted into slit 8b as shown by directional arrow A. After adhesive area 1b has been adhered to the backing sheet 18, flap 28 carrying adhesive 2b is then brought into adhering contact with the backing sheet. The diaper in its closed configuration around the waist is illustrated at the left side of FIG. 1.

The presence of circular openings 11 at the end of slits 8a and 8b permits the forces which are applied to the diaper when adhering or repositioning adhesive areas 1a and 1b and when adhering or repositioning flaps 27, 28, to be distributed more evenly, whereby the possibility of accidentally tearing the diaper in the region of the slits is greatly reduced.

As indicated earlier herein and as just described, the operation of closing and fastening the diaper of the present invention around the waist of the wearer can be accomplished independently of the operation of adjusting the fit of the diaper around the thighs so as to most effectively seal the diaper from undesirable leakage. With the diaper of the present invention, a movement of the user's leg in one direction will pull the diaper and elastic portion around the thigh to the same direction and cause the diaper to follow the body. There is less relative movement of the body and the diaper with respect to each other. This reduces the amount of "gapping" between the thighs of the wearer and the diaper itself so that the possibility of leakage is reduced.

Figure 3:
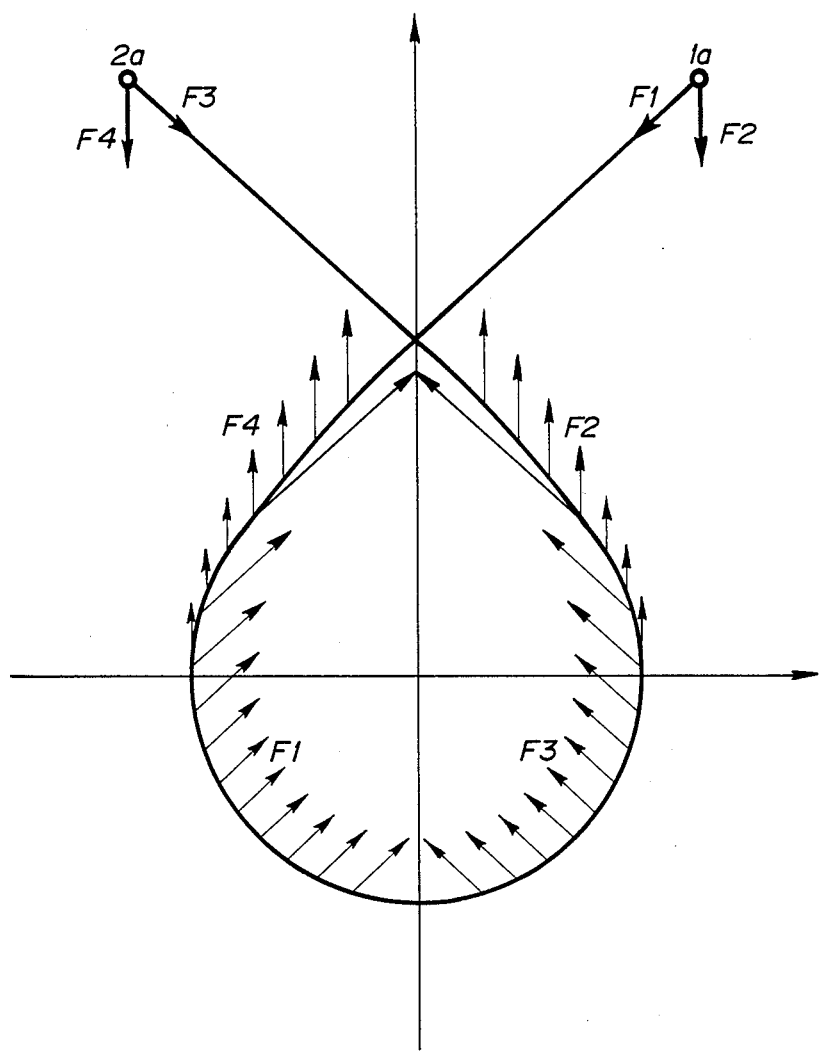
FIG. 3 is a diagram illustrating the distribution of forces on the diaper of the present invention when it is being worn.

FIG. 3 illustrates the scheme of actuating forces in such fastening and sealing system for diapers, wherein dot 1a is the adhesive region for fitting the diaper to the user's waist and legs, dot 2a is the adhesive region which provides sealing, and F1, F2, F3 and F4 are possible exertions applied on the adhesive system.

The two adhesive areas on each side of the closed diaper form two fixation dots off-positioned from the vertical axis of the thigh aperture, thus preventing the diaper from rotating around the adhesive dot and creating radial forces which tend to better fit the diaper to the body.

Modifications can be made in the invention without departing from the principles thereof. For example, slits 8a and 8b and adhesive areas 2a and 2b can be arranged near upper edge 5 of diaper 7 and areas 1a and 1b can be arranged near lower edge 6 of the diaper.

Diaper 7 can be the kind which is curved inwardly at the central regions of side edges 15 and 16 (as illustrated in FIG. 2) or, if desired, can be rectangular in overall shape.

What is claimed is:

1. A disposable diaper comprising:
    a liquid impermeable backing sheet;
    a liquid permeable covering sheet, said covering sheet having a surface which contacts the body of the wearer when the disposable article is in use;
    an absorbent core disposed between said backing sheet and said covering sheet;
    an upper edge;
    an upper marginal portion adjacent said upper edge;
    a lower edge;
    a lower marginal portion adjacent said lower edge;
    a pair of side edges, each of said side edges having a side marginal portion adjacent thereto;
    a transverse axis lying between said upper edge and said lower edge and a longitudinal axis lying between said side edges; said transverse and longitudinal axes being mutually perpendicular and intersecting in a central region of the disposable article a first upper corner in the region where said upper edge meets a first of said side edges;

a second upper corner in the region where said upper edge meets the second of said side edges;

said backing sheet being secured to said covering sheet in said marginal portions;

a first area of pressure sensitive adhesive applied to said liquid permeable covering sheet at said first upper corner;

a second area of pressure sensitive adhesive applied to said liquid permeable covering sheet at said second upper corner;

a third area of pressure sensitive adhesive applied to a first of said side marginal portions and spaced a distance upwardly from said lower edge toward said transverse axis;

a fourth area of pressure sensitive adhesive applied to the other of said side marginal portions and spaced a distance upwardly from said lower edge toward said transverse axis;

all of said areas of pressure sensitive adhesive being applied to the body-contacting surface of said liquid permeable covering sheet;

and a pair of slits, the first of said slits extending inwardly of said diaper and toward said transverse axis from a point on a first of said side edges which lies between said third area of pressure sensitive adhesive and the point of juncture of said first side edge and said lower edge, the second of said slits extending inwardly of said diaper and toward said transverse axis from a point on the other of said side edges which lies between said fourth area of pressure sensitive adhesive and the point of juncture of said other side edge and said lower edge.

2. A disposable diaper according to claim 1 wherein the distance between said lower edge and the point where said first and second slits meet said first and second side edges, respectively, is at least equal to the length, measured parallel to said longitudinal axis, of said first and second areas of pressure sensitive adhesive areas.

3. A disposable diaper according to claim 1 wherein said slits terminate in a circular opening.

4. A disposable diaper according to claim 1 wherein said slits are arcuate in configuration.

5. A disposable diaper according to any one of claims 1 to 4 wherein said upper margin comprises an elastic element.

6. A disposable diaper according to any one of claims 1 to 4 wherein said upper margin comprises an elastic element and an elastic element is provided in the central portions of said side margins.

* * * * *